(12) United States Patent
Banko

(10) Patent No.: US 6,299,591 B1
(45) Date of Patent: Oct. 9, 2001

(54) PHACOEMULSIFICATION HANDPIECE, SLEEVE, AND TIP

(75) Inventor: William Banko, Mamaroneck, NY (US)

(73) Assignee: Surgical Design Corporation, Long Island City, NY (US)

( * ) Notice: Subject to any disclaimer, the term of this patent is extended or adjusted under 35 U.S.C. 154(b) by 0 days.

(21) Appl. No.: 09/100,139

(22) Filed: Jun. 19, 1998

Related U.S. Application Data

(60) Continuation of application No. 08/664,250, filed on Jun. 7, 1996, now Pat. No. 6,159,175, which is a division of application No. 08/458,409, filed on Jun. 2, 1995, now abandoned, and a division of application No. 08/660,287, filed on Jun. 7, 1996, now Pat. No. 5,725,495, and a division of application No. 08/664,239, filed on Jun. 7, 1996, now Pat. No. 5,741,226, and a division of application No. 08/660,284, filed on Jun. 7, 1996, now Pat. No. 5,743,871.

(51) Int. Cl.[7] .................................... A61B 17/20
(52) U.S. Cl. .............................. 604/22; 604/44; 604/524; 606/107; 606/169
(58) Field of Search ................................. 604/22, 27, 35, 604/44, 524; 606/107, 169

(56) References Cited

U.S. PATENT DOCUMENTS

| | | | |
|---|---|---|---|
| 4,493,694 | * | 1/1985 | Wuchinich . |
| 4,676,229 | * | 6/1987 | Krasicki et al. . |
| 4,832,683 | * | 5/1989 | Idemoto et al. . |
| 4,869,715 | * | 9/1989 | Sherburne . |
| 4,900,314 | * | 2/1990 | Quackenbush . |
| 5,282,786 | * | 2/1994 | Ureche . |
| 5,318,032 | * | 6/1994 | Lonsbury et al. . |
| 5,334,169 | * | 8/1994 | Brown et al. . |
| 5,484,398 | | 1/1996 | Stoddard . |
| 5,562,609 | * | 10/1996 | Brumbach et al. . |
| 5,674,208 | * | 10/1994 | Berg et al. . |

* cited by examiner

Primary Examiner—Mark Bockelman

(57) ABSTRACT

A phacoemulsification instrument that significantly reduces infusion fluid leakage by providing a silicone sleeve with a built in reinforcing member. Also, the sleeve has only a single infusion hole in order to provide better infusion fluid flow without causing turbulence in the eye. In addition, the present invention provides either a valve or a variable aperture aspiration tube in order to regulate the aspiration rate. Also, the present invention includes a single aspiration hole at the tip in order to amplify flow coming to the tip. To assist in cataract removal, the tip may be provided with a variety of different barrier and baffle configuration. A handpiece includes a variable capacity reservoir in the infusion line to account for surges in the aspiration line. The needle includes steps, angles and barriers to focus ultrasonic energy to aid in emulsifying nuclear tissue and to aid in pushing emulsified material in the direction of aspiration flow. A compressible sleeve is rotatably coupled to the handpiece to permit the handpiece and needle to be manipulated to a limited extent in the axial direction and rotated freely about the longitudinal axis while the sleeve remains stationary with respect to the cornea.

19 Claims, 18 Drawing Sheets

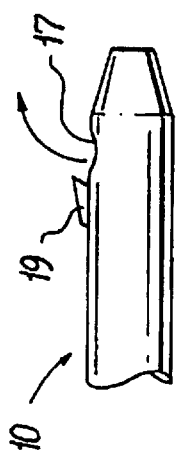
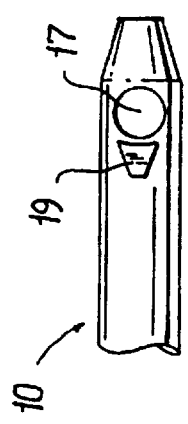
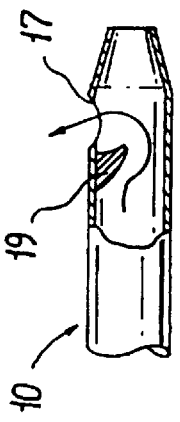
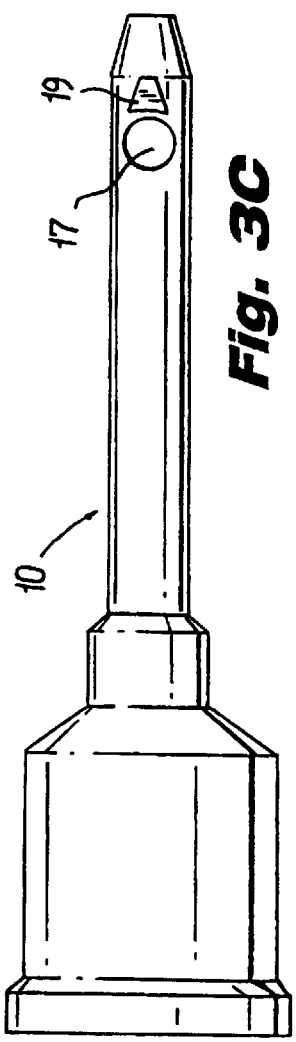
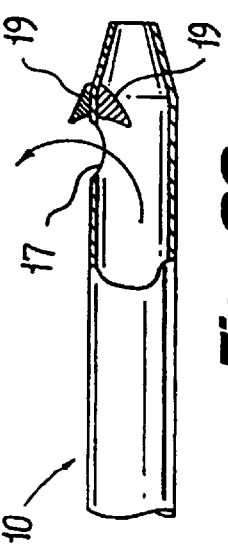

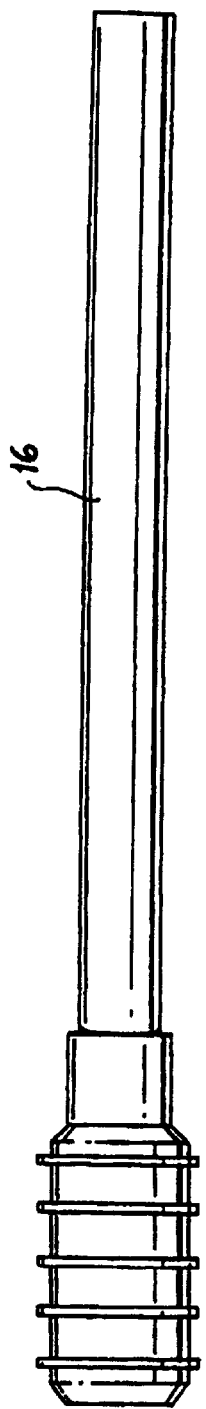
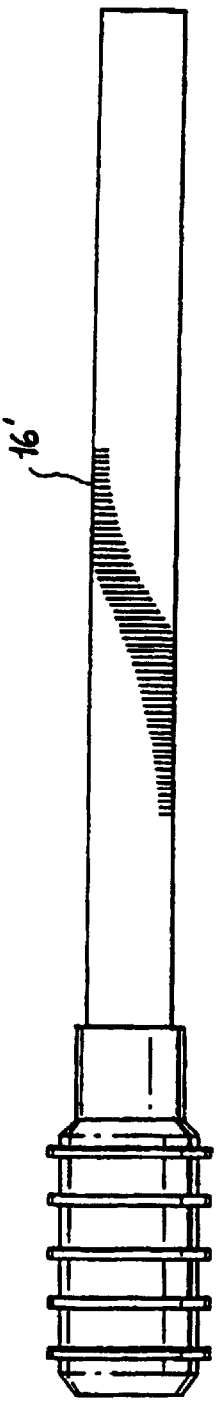
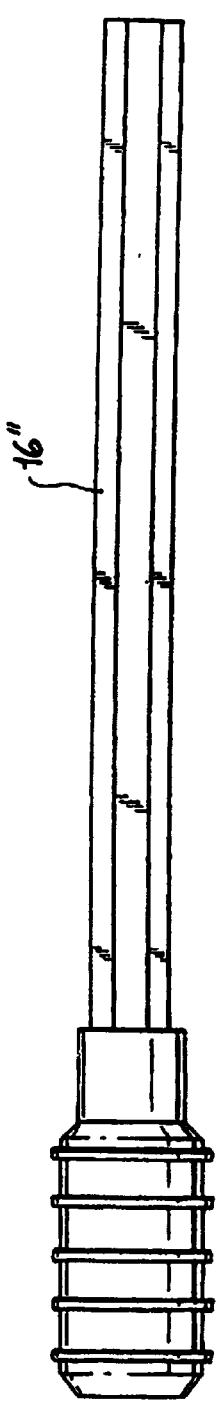
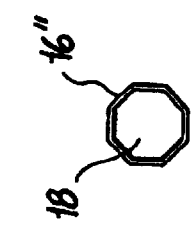

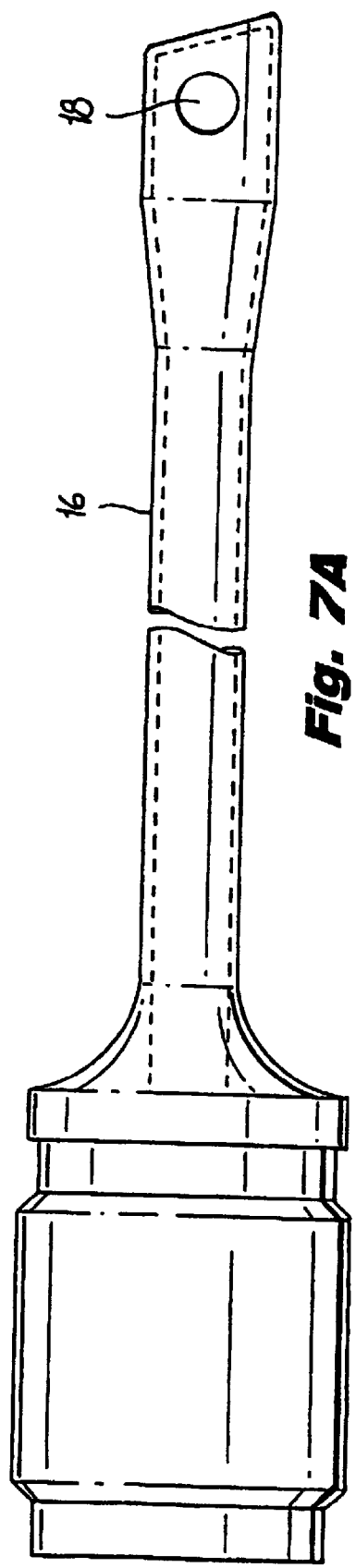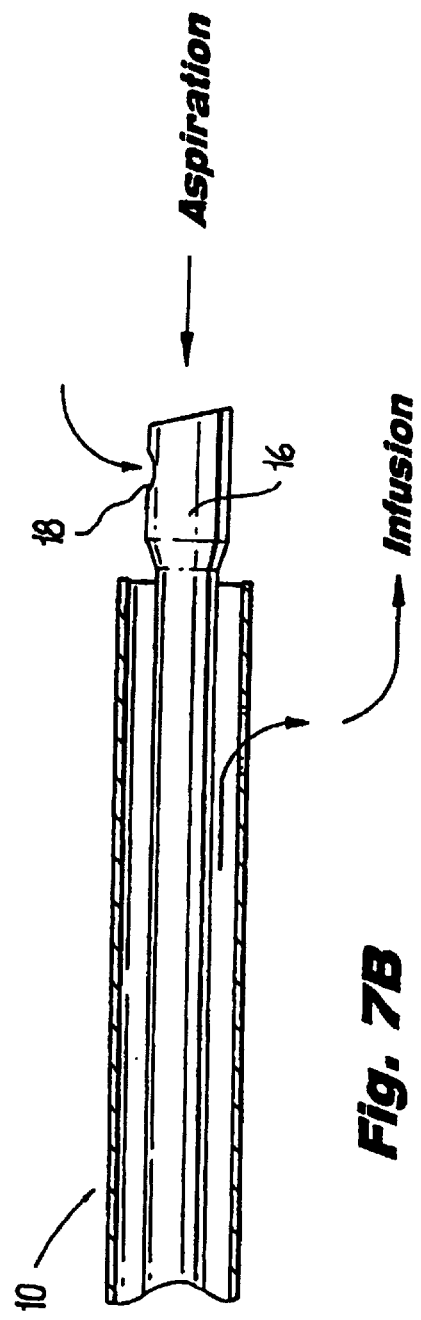
Fig. 7A
Fig. 7B

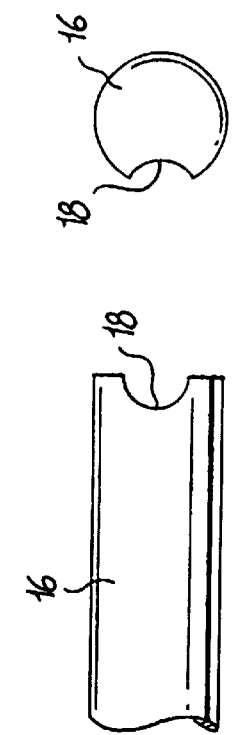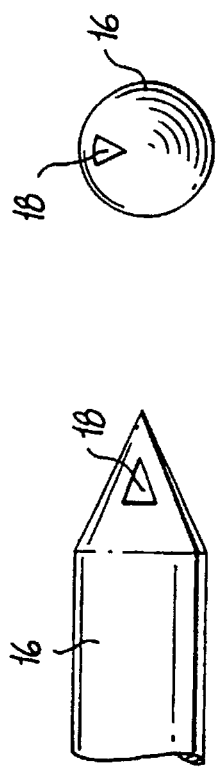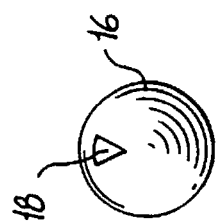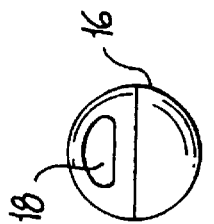
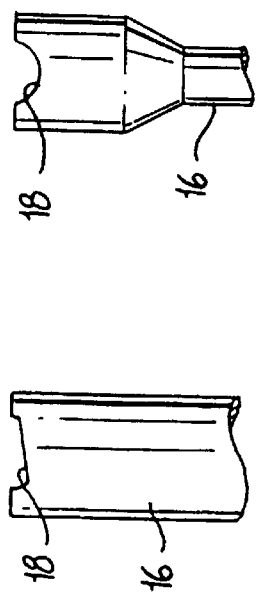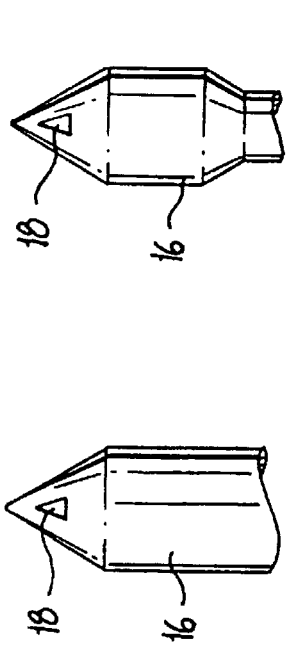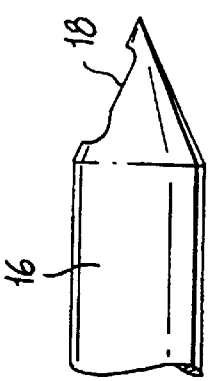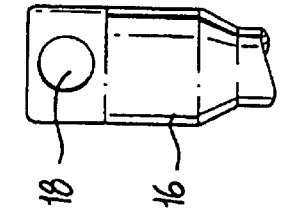

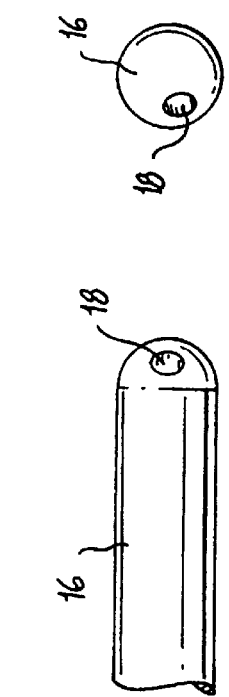
Fig. 11A
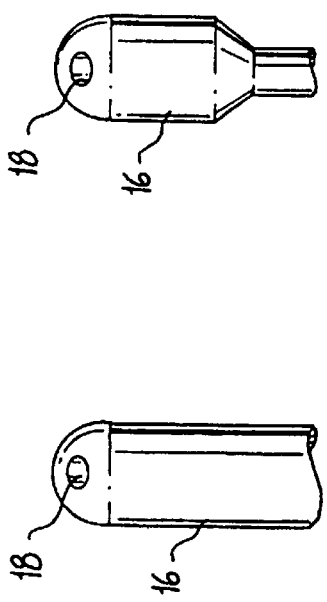
Fig. 11B
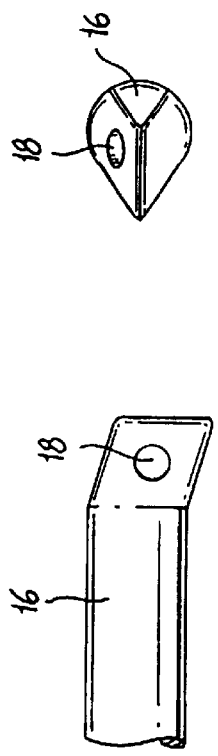
Fig. 11C
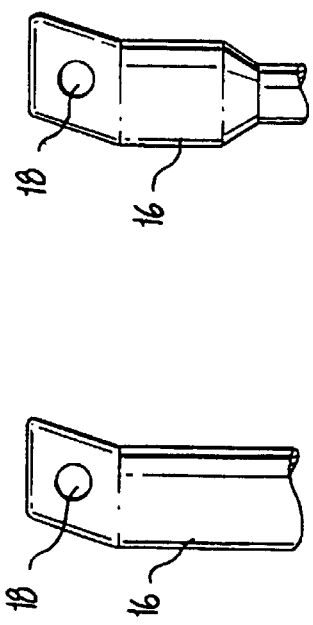
Fig. 11D
Fig. 12A
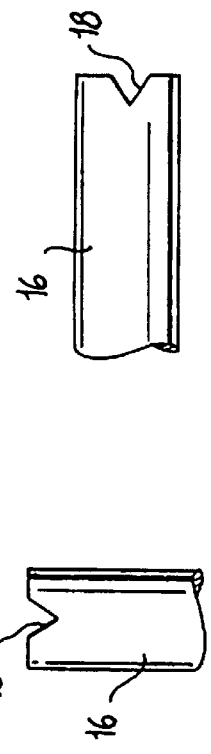
Fig. 12B
Fig. 12C
Fig. 12D
Fig. 13A
Fig. 13B
Fig. 14A
Fig. 14B

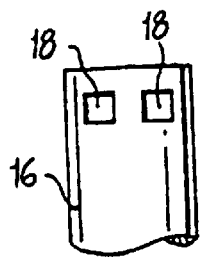
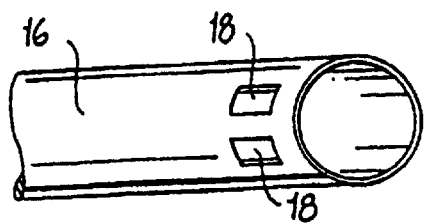
Fig. 23A  Fig. 23B
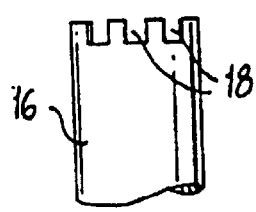
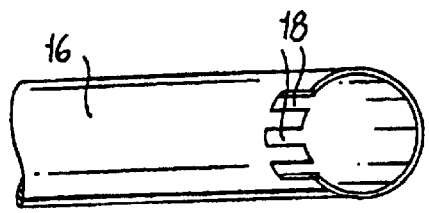
Fig. 24A  Fig. 24B
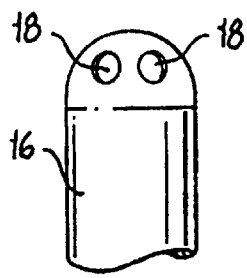
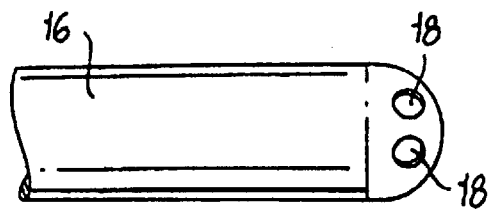
Fig. 25A  Fig. 25B
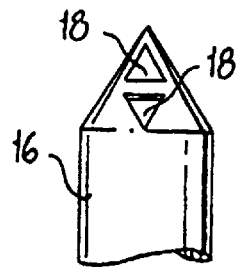
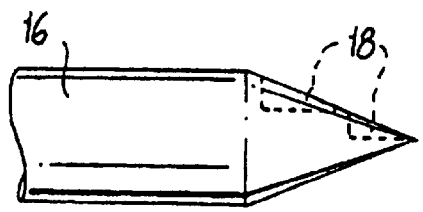
Fig. 26A  Fig. 26B
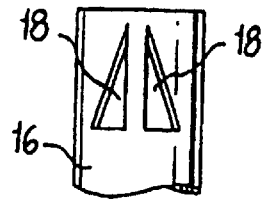
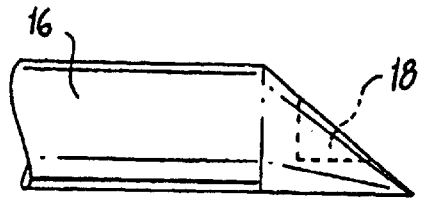
Fig. 27A  Fig. 27B

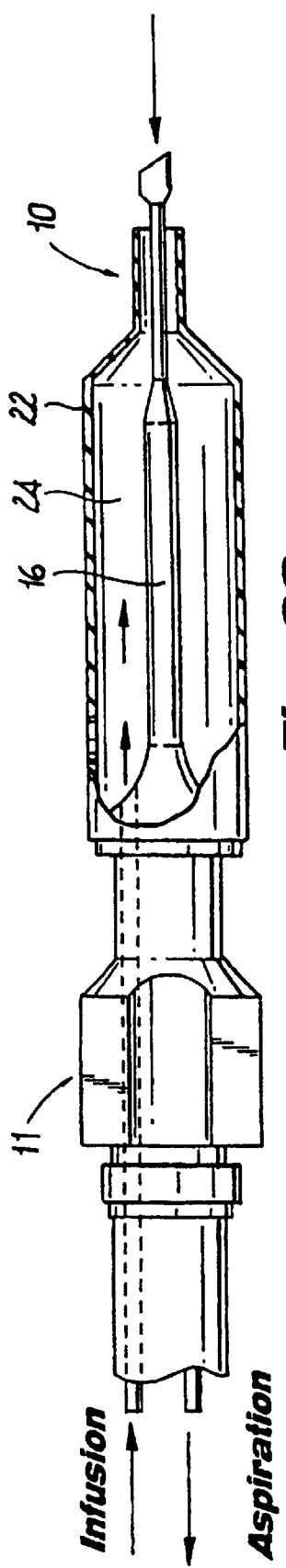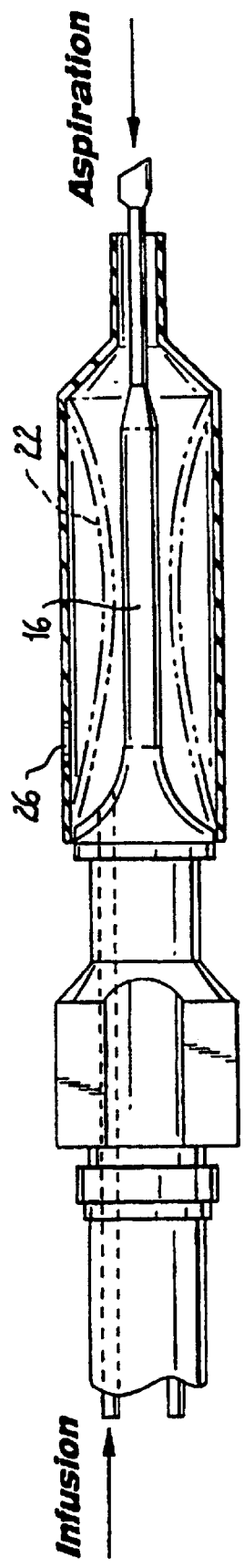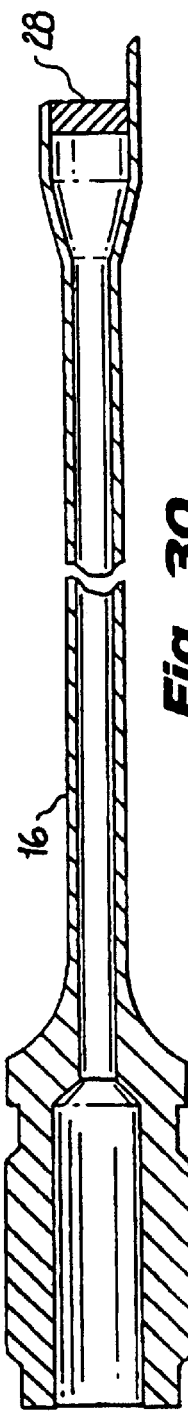

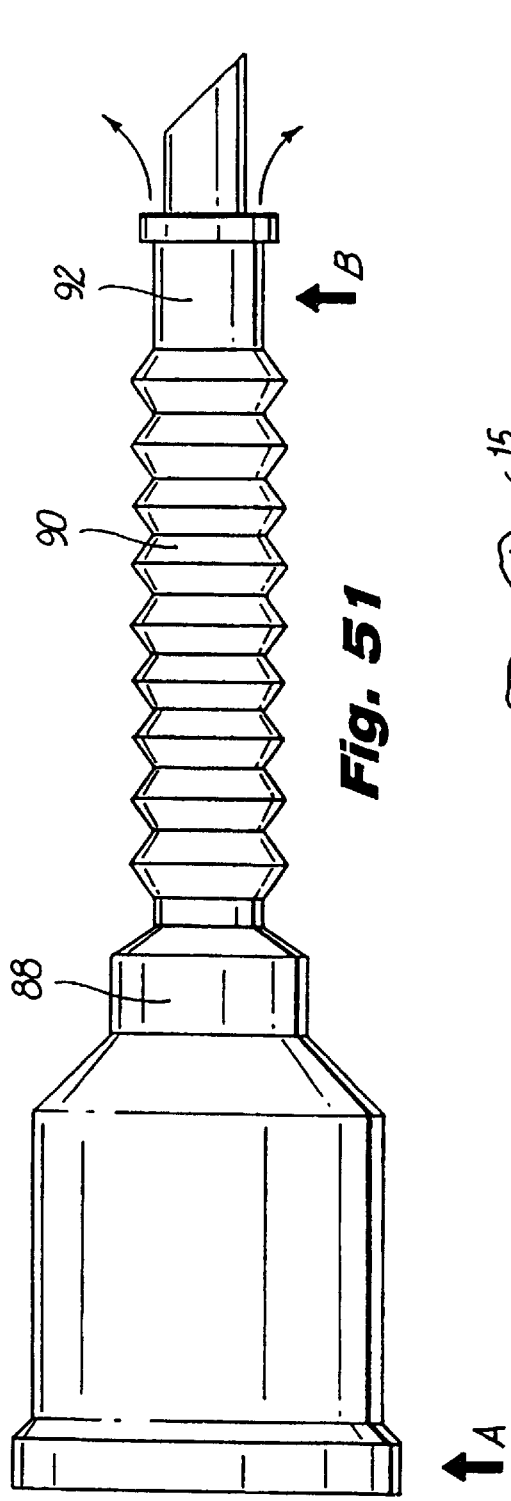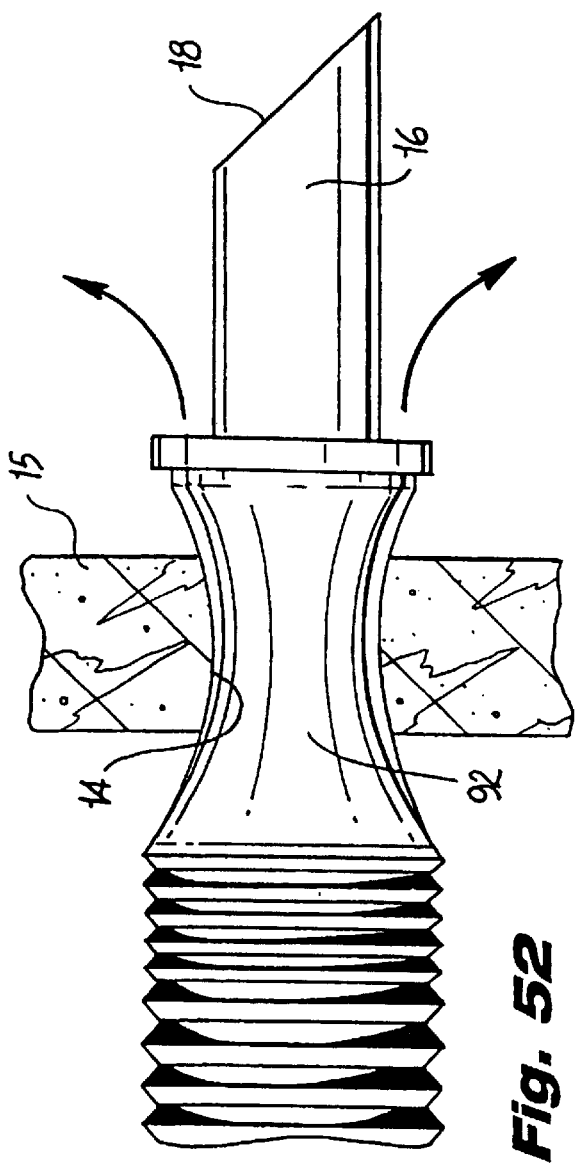

PHACOEMULSIFICATION HANDPIECE, SLEEVE, AND TIP

This is continuation application Ser. No. 08/664,250, filed Jun. 7, 1996, now U.S. Pat. No. 6,159,175 which is a division of application Ser. No. 08/458,409 filed Jun. 2, 1995, now abandoned other divisions of application Ser. No. 08/458,409 are:

Ser. No. 08/660,287 filed Jun. 7, 1996 now U.S. Pat. No. 5,725,495 granted Mar. 10, 1998

Ser. No. 08/664,239 filed Jun. 7, 1996 now U.S. Pat. No. 5,741,226 granted Apr. 21, 1998 and Ser. No. 08/660,284 filed Jun. 7, 1996 now U.S. Pat. No. 5,743,871 granted Apr. 28, 1998.

BACKGROUND OF THE INVENTION

1. Field of the Invention

The present invention relates to an apparatus for surgically removing a cataractous lens from a human eye. More specifically, the present invention relates to an improved flexible phacoemulsification sleeve with a built in reinforcing member, a phacoemulsification sleeve with a barrier connected to the tip to direct infusion from a single or multiple infusion hole while permitting minimal or no occlusion, a tip for a phacoemulsification handpiece with different configuration of barriers and baffles to increase cutting and a side opening to amplify fluid flow to the tip, a phacoemulsification handpiece with a valve to regulate the rate of evacuation, a phacoemulsification handpiece with a variable aperture aspiration line, a sleeve that includes a built-in reservoir, a stepped inside ultrasonic needle to direct ultrasonic waves to enhance emulsification and aspiration, and a sleeve that is compressible and rotatably connected to the handpiece in a fluid tight manner.

2. Discussion of the Related Art

The human eye contains a lens which focuses on the retina, the sensory membrane that lines the eye and receives the image formed by the lens. Through trauma, age, disease, mutation, or naturally occurring processes, the natural crystalline lens may become opaque or cloudy and thus cease to clearly transmit and focus light. This clouding of the lens is known as a cataract.

In the last few decades, techniques have been developed to surgically remove the cataract lens and replace it with an artificial or intraocular lens. This cataract lens extraction process may be performed by a number of medically recognized techniques. One of the more well known and widely used techniques is phacoemulsification.

The phacoemulsification procedure involves placing two concentric tubes through a corneal incision of approximately three millimeters. This incision is made in the region of the limbus where a colored portion of the eye meets a white portion of the eye. The incision can also be made in the cornea. The inner tube, known as a needle, is ultrasonically vibrated such that its vibrating tip member operates to emulsify the hard nuclear material of the cataract lens.

In this type of surgery, the vibrating inner tube also functions as an aspirator so that the emulsified cataract lens material may be aspirated out of the eye. The outer tube, known as a sleeve, functions as an irrigator allowing for inflow of saline fluid into the eye. The saline fluid serves several purposes. First, the presence of the saline fluid prevents the cornea from collapsing as the lens material is emulsified and aspirated. Second, the saline aids in the aspiration of the cataract lens material out of the eye. The concentric tubes of a handpiece of the system are attached to an external power source, fluid source, and vacuum source, which provide for controlled ultrasonic vibration, inigation, and suction.

The importance of infusing a fluid into the eye during cataract surgery cannot be understated. The fluid infusion serves to maintain the eye in an inflated, pressurized condition during cataract removal. However, there are several factors that increase the difficulty with which the eye structure can be maintained and supported in an inflated, pressurized condition during cataract surgery.

One of the prevalent causes of diminished inflation of the eye during cataract surgery is leakage of fluid from the eye. This leakage normally occurs between the edges of the incision and the exterior surface of the infusion sleeve. This leakage can have significant deleterious consequences to the success of the surgery being performed.

One of the adverse consequences of fluid leakage is that there is a tendency for the eye to deflate during the operation. This deflation causes certain tissues within the eye to collapse on each other or on the surgical instrument that extends into the eye. The tissues most likely to be damaged from the consequences of such fluid loss are the cornea, the iris, and the lens capsule, which surround the cataract. One method of counteracting this fluid leakage is to increase the amount of fluid flow in order to maintain proper inflation of the eye. However, this approach is not a satisfactory solution to the problem of fluid leakage from the eye because the greater the infusion of fluid into the eye, the more the flow becomes rapid and even turbulent. This can cause damage to the cornea, especially to the fragile cells that line the inside of the cornea.

The fragile cells that line the inside of the cornea are known as corneal endothelitim and cannot be regenerated by the eye. Once these cells are damaged or destroyed, they cannot be repaired or replaced by human regeneration. Also, damage to the corneal endothelium can cause permanent damage to the cornea, resulting in corneal clouding and decreased vision, all of which may require a corneal transplant. It should be noted that the most common cause of corneal clouding and corneal transplantation in the United States today are complications from eye surgery for cataract removal and intraocular lens insertion.

As a result, the phacoemulsification procedure would be significantly improved if corneal damage as a result of fluid flow leakage during intraocular surgery could be reduced or eliminated.

Most infusion sleeves used for phacoemulsification or intraocular surgery are made of silicone or silicone-type material. However, the use of silicone sleeves presents significant problems with respect to fluid leakage between the incision edge in the eye and the exterior surface of the silicone infusion sleeve. This is due to the fact that the incision in the eye must be larger than the silicone infusion sleeve, since the silicone infusion sleeve is made from a soft, compressible material and cannot be used safely when inserted through an incision in the eye where there is a minimal amount of clearance between the incision and the exterior of the silicone infusion sleeve.

When there is a minimal amount of clearance between the exterior of the silicone infusion sleeve and the incision in the eye, the incision tends to compress the non-rigid silicone sleeve against the vibrating tip, resulting in a relative rubbing movement between the silicone sleeve and the vibrating tip. This rubbing movement generates undesirable heat as the needle in the tip is vibrated at relatively high frequencies. The heat thus generated is extremely undesirable and can result in thermal burns and shrinkage of ocular tissue surrounding the silicone infusion sleeve.

The burning and shrinkage of ocular tissue is a serious problem that has sight threatening implications. The rubbing of the infusion sleeve against the vibrating needle also constricts the path for fluid flow into the eye, thus impeding efforts to keep the eye pressurized and inflated.

In an attempt to reduce the infusion fluid leakage and the deleterious effects that can be caused by the undesirable friction, some infusion sleeves have been constructed from rigid non-compressible materials. Generally, these materials have consisted of teflon or metallic-based compositions. These rigid non-compressible infusion sleeves have been somewhat successful in solving the constriction problems in the fluid flow path between the distal end of the infusion sleeve and the vibrating tip. In addition, these sleeves have also reduced the heat generation and thermal burns associated with silicone-type sleeves.

While rigid, non-compressible sleeves are capable of being inserted through smaller incisions that reduce leakage through the clearance between the rigid, non-compressible sleeve and the incision, there is still a significant amount of leakage. The primary cause of this remaining leakage is that the cross section of the rigid, non-compressible sleeve does not match the shape or contour of the eye incision. As a result, there are fairly substantial gaps between the rigid, non-compressible sleeve exterior surface and the eye incision. This is due to the fact that the collagen fiber structure of the cornea resists deformation and does not readily assume the shape of the infusion sleeve.

Other attempts to reduce the infusion fluid leakage and associated side effects, such as the one disclosed in U.S. Pat. No. 5,084,009 to Mackool, include using a double sleeve system with the inner sleeve being made from a rigid material such as teflon and the outer sleeve being made from a flexible material such as silicone. However, there are still many problems with this type of approach. For example, a double sleeve system requires a stepped titanium needle. The needle 106 is not illustrated as being stepped in the '009 patent, however, only the most distal end of the needle is illustrated. In practice, this double sleeve arrangement requires a stepped titanium needle. Additionally, this arrangement requires more parts (i.e., teflon sleeve inside and a silicone outside sleeve). The teflon sleeve must be cut along its entire axial length to be placed around the posterior part of the needle, because the needle contains a threaded posterior part and a stepped anterior part. Since both the thread and step are larger than the diameter of the sleeve, the only way to get the teflon sleeve on the needle is to cut the sleeve along its entire length.

Additionally, with respect to the phacoemulsification sleeve, prior art devices use two infusion ports in order to improve fluid flow. However, the use of two ports or holes tends to cause turbulence in the eye. Thus, there is a need for improved flow sleeves that reduce or completely eliminate turbulence in the eye and direct infusion away from the aspiration hole.

As to the handpiece used in phacoemulsification procedures, it should be recalled that the inner tube is used for aspiration, while the outer tube is used for irrigation. During surgery, it is often desirous to change the rate of aspiration. However, if the rate of evacuation or aspiration is too high, undesirable intra-ocular surges may occur. Thus, there exists a need for a phacoemulsification handpiece, where the aspiration can be reliably and accurately controlled.

Regarding the tip or needle that performs the actual cutting away of the nuclear material as it is ultrasonically vibrated, different designs have been proposed in order to increase cutting. However, these designs suffer from emitting ultrasonic energy in the eye and not emulsifying efficiently.

SUMMARY OF THE INVENTION

It is therefore an object of the present invention to provide a phacoemulsification sleeve that significantly reduces infusion fluid leakage by providing a silicone sleeve with a built-in reinforcing member. It is also an object of the present invention to provide a phacoemulsification sleeve with barriers or vanes or steps that direct infusion fluid flow away from the aspiration hole and minimize turbulence in the eye.

It is yet a further object of the present invention to provide a, phacoemulsification handpiece having a valve which will close when the rate of evacuation is too high, in order to prevent intraocular surges. A still further object of the present invention is to provide a phacoemulsification handpiece with a variable capacity reservoir in the infusion line to vary the amount of infusion flow to account for surges in the aspiration line tubing. The surges in the aspiration line would decrease the intraocular pressure.

It is a further object of the present invention to provide a phacoemulsification needle with a single aspiration hole on one side to amplify the flow coming to the tip. It is a further object to provide a needle with different configuration of barriers, baffles, steps in order to increase cutting and suction effect within the needle.

Additional objects and advantages of the invention will be set forth in the description which follows, and in part will be obvious to those skilled in the art from the description itself, and further will be appreciated by those practicing the invention and using the resulting phacoemulsification device.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIGS. 3A–G are a top and side views of a phacoemulsification sleeve with a single infusion hole with internal or external steps to direct infusion;

FIGS. 6A–F are side and front views showing various shaped needles;

FIGS. 7A–B are side views of a phacoemulsification needle with a hole on one side and a single infusion hole in the sleeve;

FIGS. 8A–D, 9A–D, 10A–D, 11A–D, 12A–D show different shapes of the emulsification end of the needle;

FIGS. 13A–B, 14A–B, 15A–B, 16A–B, 17A–B show different sizes and shapes of aspiration holes;

FIGS. 21A–B, 22A–B, 23A–B, 24A–B, 25A–B, 26A–B and 27A–B show multiple aspiration holes;

FIG. 28 is a side view of handpiece assembly including a silicone membrane which acts as a reservoir chamber for infusion fluid;

FIG. 29 is a side view of the handpiece assembly of FIG. 28 with the silicone membrane being shown collapsed during an aspiration surge;

FIG. 30 is a side view of a phacoemulsification needle showing one of the different configurations of barriers and baffles;

FIG. 51 is a side view of a compressible sleeve according to the present invention; and FIG. 52 is a anterior view of the compressible sleeve inserted into an incision in the cornea.

DETAILED DESCRIPTION OF THE PREFERRED EMBODIMENTS

Figure 1A:
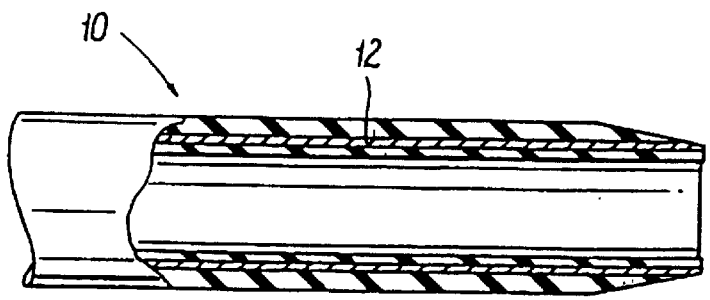
FIGS. 1A and 1B are cross-sectional and front views, respectively, of the of the silicone phacoemulsification sleeve with a built-in reinforcing member.
Figure 1B:
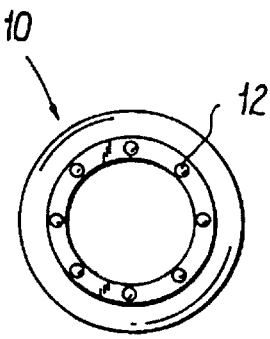

The phacoemulsification sleeve 10 of the present invention is a silicone sleeve with a built-in reinforcing member. The sleeve can be used in an ultrasonic handpiece similar to the one disclosed in Applicant's commonly owned U.S. Pat. No. 5,242,385 to Strukel, the disclosure of which is hereby incorporated by reference. The sleeve is essentially a silicone sleeve of approximately 0.005 inches thickness with an overall dimension of approximately 1.0 inch, as shown in FIG. 1. In a preferred embodiment of the present invention, interwoven in the silicone walls of the sleeve are strands of teflon or metallic-based material 12 to provide a rigid frame for the silicone walls. In an alternative embodiment, the teflon or metallic material is in the form of a spiral or single strand that are embedded in the silicone walls of the sleeve. Alternatively, the sleeve could be impregnated with strands of fiber glass or kevlar which will also act as a reinforcing member. Of course, the sleeve could be reinforced with any number of different devices so long as the reinforcing member has a higher durometer (i.e., is harder) than the silicone.

Figure 2A:
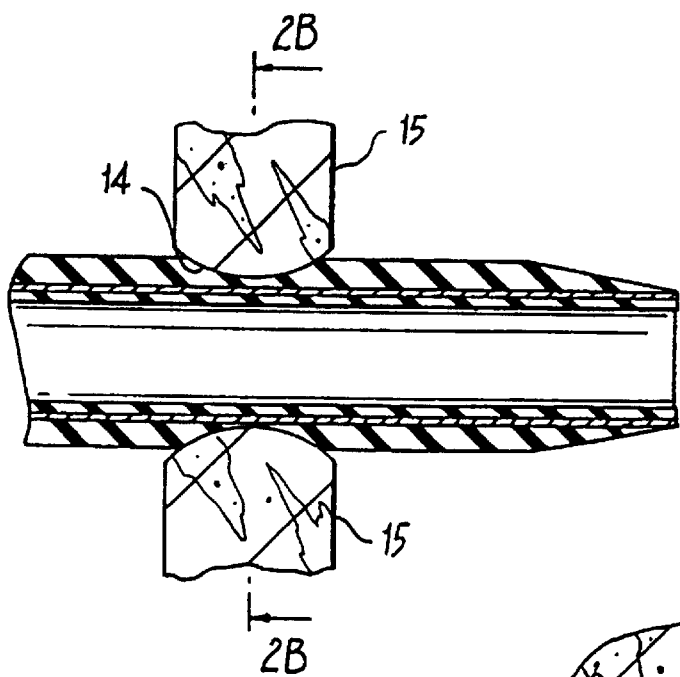
FIGS. 2A and 2B are cross-sectional and front views respectively of the silicone sleeve inserted through an incision in the cornea.
Figure 2B:
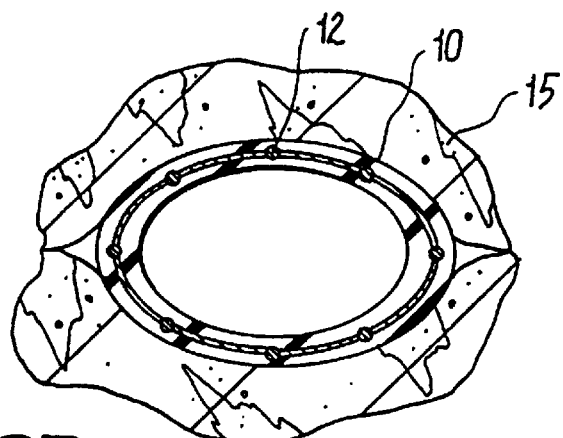

The resulting sleeve has the advantages of both a rigid sleeve and a compressible sleeve, without suffering from the deleterious effects that plague each individual approach. By having a relatively compressible outer layer, the sleeve of the present invention is able to be deformed slightly in order to match the shape or contour of the eye incision 14, in the cornea 16, as illustrated in FIGS. 2A–2B. However, because the present sleeve has a built-in rigid frame, it is not deformable to the extent that a completely compressible silicone sleeve would be deformed. This reduction in deformation avoids the prior art disadvantages such as rubbing between the silicone sleeve and the vibrating tip that results in heat generation and thermal burns, as well as constriction of the fluid flow path into the eye.

During phacoemulsification the ultrasonic needle radiates ultrasonic energy from its tip into the eye and pushes fluid and lens material away from the tip. The flow through the aspiration port brings the material to the tip. The ideal effect is to efficiently bring the cataract to the tip, completely emulsify the cataract and aspirate the emulsified cataract through the ultrasonic needle. To enhance the emulsification, surfaces can be added to the inside or outside of the ultrasonic needle which will direct ultrasonic waves in the desired direction.

Ultrasonic needles are currently manufactured of titanium and have a generally circular cross-section as illustrated in FIGS. 6A and 6B. The needles 16 are used for phacoemulsification and for cutting and removing tissue during surgery. Other cross sectional shapes such as a triangle, as illustrated in FIGS. 6C and 6D, or polygonal shapes, such as a hexagon, as illustrated in FIGS. 6E and 6F can be used to improve the cutting and emulsification properties of the needle. In addition, the use of non-circular cross-sectional needle shapes will provide a flat surface which may be a more practical surface to work with to weld or machine other surfaces to the needle. These additional surfaces would then vibrate with the needle. The surfaces, which will generate ultrasonic energy, can be arranged so that the ultrasonic energy is directed in the preferred areas.

Conventionally, ultrasonic needles have been manufactured having circular openings at the distal end. This opening is known as the aspiration hole 18. The aspiration opening within the needle is simply made by drilling a throughbore in the titanium shaft. An alternative method of forming the needle 16 would be to not drill the hole completely through the needle but to leave the distal end of the needle closed. In other words, a blind bore would be drilled into the needle. An aspiration hole 18 would then be provided on the side of the needle 16. An advantage of providing the aspiration hole 18 in the side of the needle is that the distal axial end of the needle can then be made, by machining, to any desired shape, such as a flat surface or a slanted wedge shape, as illustrated in FIGS. 7A and 7B. Numerous other end configurations are illustrated in FIGS. 8A–27B. A further advantage of placing the aspiration hole 18 in the side of the needle 16 is that the hole 18 can be placed anywhere along the needle surface and can be sized and/or shaped depending on the needs of the user. A further advantage is that with the closed tip, additional ultrasonic energy will be emitted from the closed tip surface which will aid in emulsifying tissue. The specific shape of the tip, including the angle, concavity, convexity, etc. can be designed to selectively focus ultrasonic energy. Additionally, surface area can be designed to emit either a large or small amount of ultrasonic energy. Generally, the larger the surface area, the larger the amount of ultrasonic energy which will be generated. In certain portions of the tip it is important to emit less ultrasonic energy to reduce the likelihood of breakage to the posterior capsule.

The ultrasonic waves radiate from the metallic surfaces. Accordingly, the surface of the tip could be modified so that it will intensely focus the ultrasonic energy to emulsify tissue. However, if the surface is designed to focus low ultrasonic energy, that surface can be used to selectively clean tissue without the emulsification of tissue taking place. Additionally, if the ultrasonic energy is finely focused, that energy can be used to cut the tissue. Accordingly, the surfaces of the tip can be designed to be tissue specific in its ability to focus ultrasonic energy. Various embodiments of ultrasonic needles 16 are illustrated in FIGS. 7A–27B. Each of these needle embodiments have holes of various sizes and shapes and various needle surfaces to vary the amount of focusing of the ultrasonic energy and the amount of aspiration through the aspiration hole 18.

As discussed above, conventional ultrasonic needles have only one aspiration port 18 which is disposed at the axial distal end of the needle. Applicants have discovered that the addition of a second aspiration port, disposed near the main aspiration port or even as part of the main aspiration port can provide numerous advantages in the use of the needle 16. FIGS. 24A and B illustrate an embodiment where the second aspiration port 18' can be disposed as being a part of the main aspiration port 18. For example, during certain uses of the needle you will want to build a vacuum in order to hold tissue at the tip. This is especially true during certain types of cataract surgery, where it is desirous to occlude the tip during either the "divide and conquer" or the "phaco chop" techniques of cataract surgery. During these techniques, it is often desirable to hold the nucleus on the phacoeneedle tip. Obviously, it will be necessary to cover both aspiration holes to build a vacuum. However, during the emulsifying of tissue in the primary port, it is often advantageous to have a secondary aspiration port available to assist in the further aspiration of the emulsified tissue.

Referring to FIGS. 3A–3F, a sleeve 10 having an infusion port 17 is illustrated. Sleeve 10 is illustrated as having baffles 19 disposed on either the interior or exterior surface adjacent to the infusion port 17 to assist in directing the flow of infusion fluid. As illustrated in FIG. 3A, the baffle 19 can be disposed on the outer portion of the sleeve 10 in an area disposed between infusion port 17 and the distal end of the sleeve 10. In FIG. 3A the baffle directs an infusion fluid away from the aspiration port. However, if desirable, the baffle 19 can be placed on the opposite side of the infusion port 17, as illustrated in FIG. 3B to direct the infusion fluid in the forward direction towards the distal end of the sleeve 10.

As illustrated in FIG. 3E, the baffle 19 can be disposed within the interior of the sleeve 10 between the infusion port 17 and the distal end of the sleeve. Alternatively, as illustrated in FIG. 3F, the baffle 19 can be disposed on the proximal side of the infusion port 17. Additionally, as illustrated in FIG. 3G, a baffle 19 can be disposed on both the exterior and interior surface of sleeve 10. As illustrated in FIG. 3G, the baffles are located on the distal side of infusion port 17. However, just as has been illustrated in FIGS. 3B, 3D and 3F, baffles 19 could be disposed on the proximal side of the infusion port 17.

Figure 4:
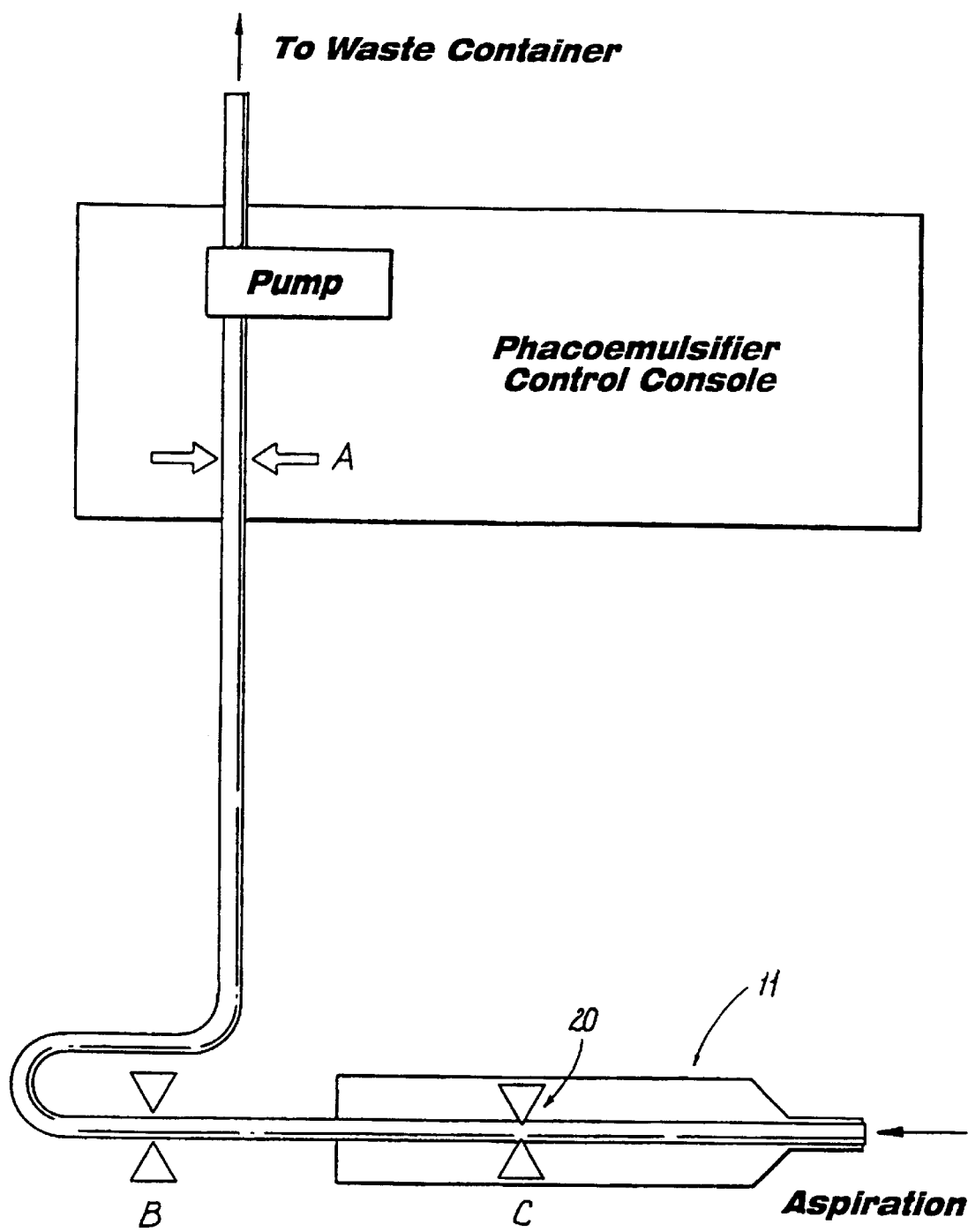
FIG. 4 is a side view of a phacoemulsification handpiece or an irrigation aspiration handpiece having a valve to constrict the aspiration line.
Figure 5:
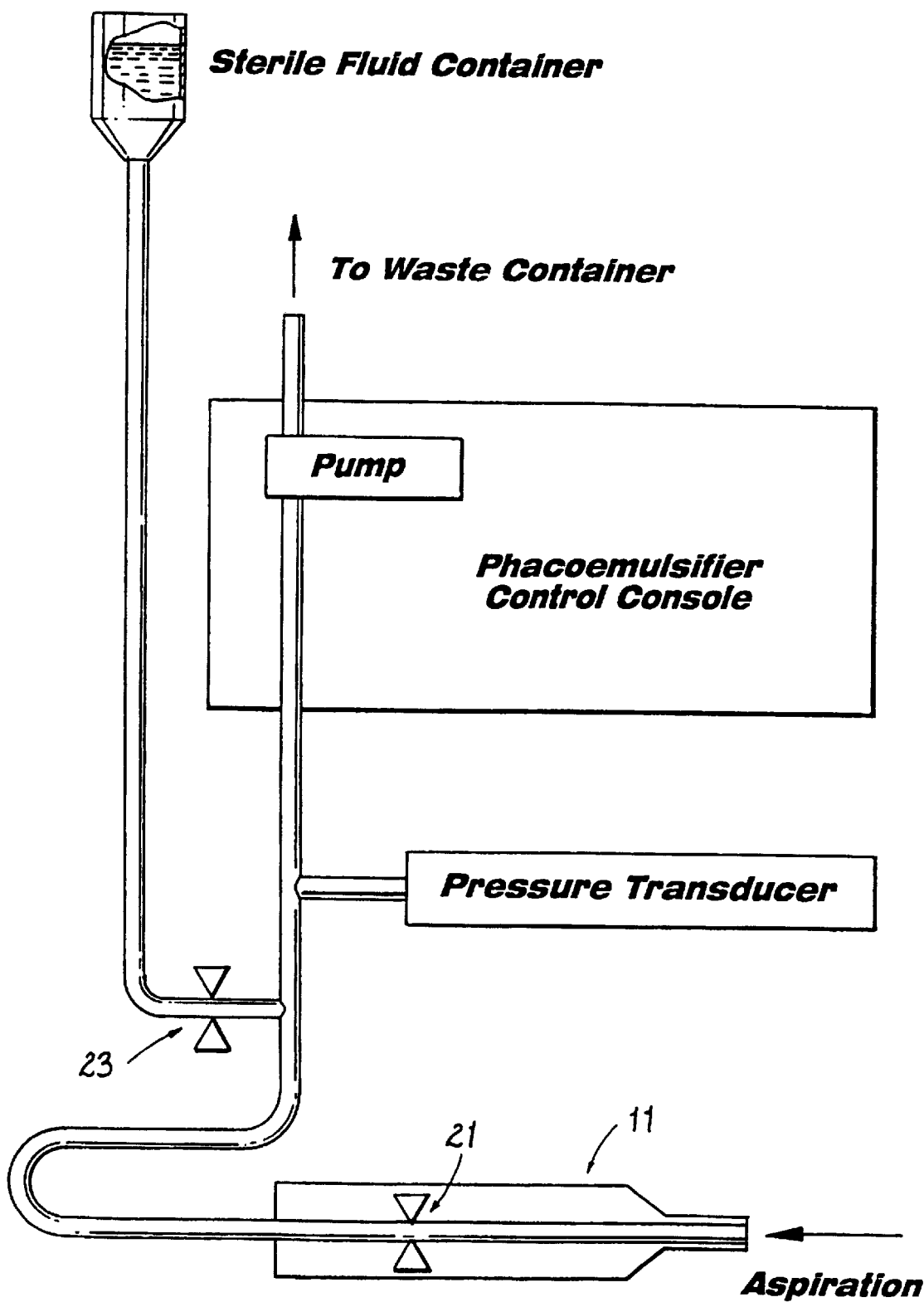
FIG. 5 is a schematical side view of a phacoemulsification handpiece with a variable aperture aspiration line.
Figure 15A:
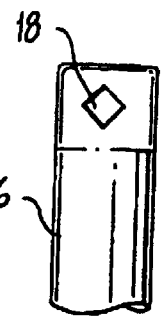
Figure 15B:
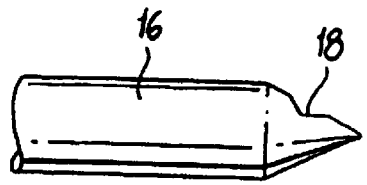
Figure 16A:
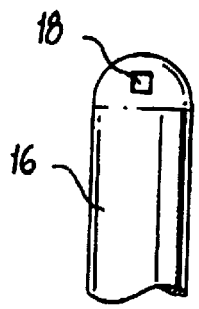
Figure 16B:
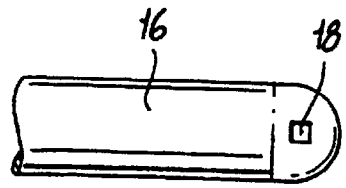
Figure 17A:
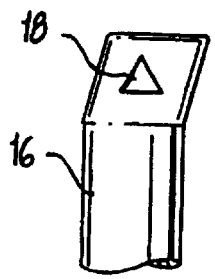
Figure 17B:
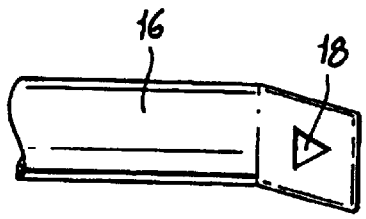
Figure 18A:
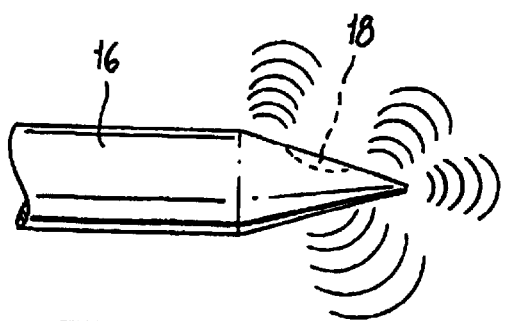
FIGS. 18A–B, 19A–B, 20A–B show concave, convex and angled surfaces which are designed to direct ultrasonic waves.
Figure 18B:
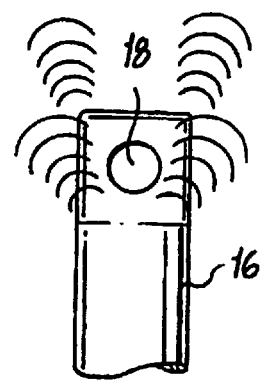
Figure 19A:
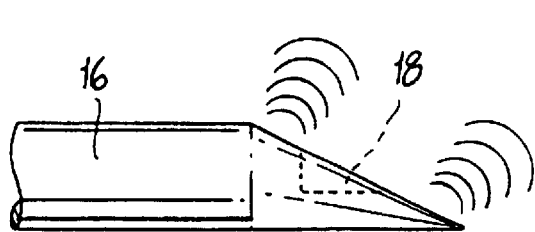
Figure 19B:
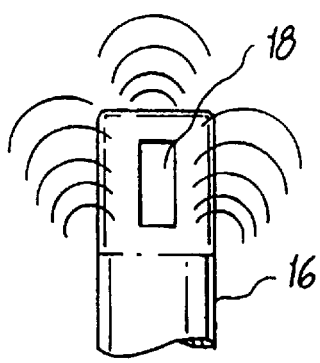
Figure 20A:
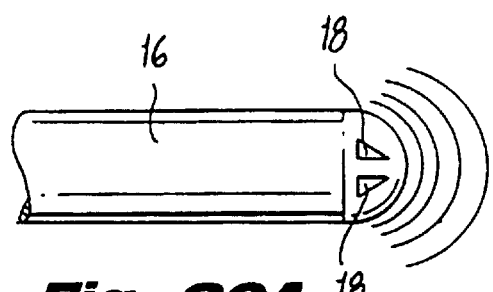
Figure 20B:
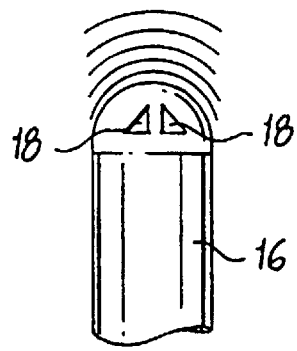
Figure 21A:
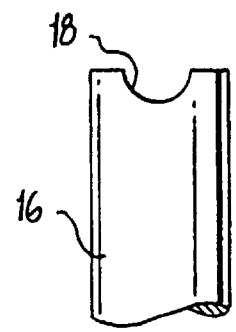
Figure 21B:
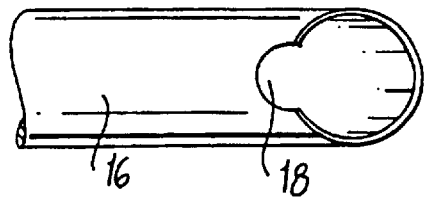
Figure 22A:
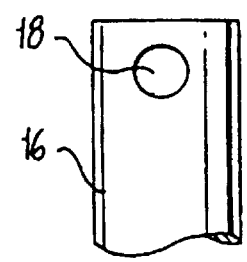
Figure 22B:
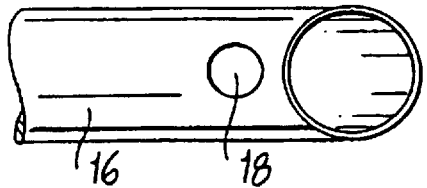

Referring now to FIGS. 4 and 5, a phacoemulsification handpiece 11 according to the present invention is shown.

The handpiece 11 has a valve 20 in the aspiration line. The function of the valve is to constrict the flexible tubing of the aspiration line to create resistance in the aspiration line. Also, the valve may be used to change the flow characteristics at the needle tip. The valve may be controlled either at the phacoemulsification machine control panel or directly at the handpiece. It should be pointed out that the valve control can be simply an on/off valve or a valve that allows for analog-type control whereby the valve can be adjusted to any precise level between completely on and completely off. In the preferred embodiment of the present invention, the valve is located at the anterior portion of the handpiece.

The handpiece of FIG. 4 has a valve 20 which is preferably controlled so that it can be adjusted to any precise level between completely on and completely off. The valve can be positioned at position C in FIG. 4 which is within the handpiece, or at position B immediately behind the handpiece or at position A, which is adjacent to the housing for the aspiration pump. The valve is controlled by a control console which receives signals from a pressure transducer (not shown) which detects the fluid pressure within the aspiration conduit. Upon the detection of the varying pressure within the aspiration line, the control console automatically actuates the valve to variably increase or decrease the cross-sectional area of the aspiration conduit to ensure substantially constant pressure within the conduit.

In the embodiment illustrated in FIG. 5, a valve 21 is disposed within the handpiece 11. This valve 21 is preferably of the type that is an on/off valve, as discussed above. Upon the detection of a pressure surge, the control console immediately sends a signal to close valve 21. Simultaneously, valve 23 is opened to release relatively high pressure fluid from a sterile fluid container into the aspiration conduit. Thereafter, the bottom valve 21 is opened, the full effect of the surge is erased and then valve 23 is closed once again. The system is then ready to detect and control the next surge within the aspiration line.

The advantages of an on/off valve, such as valve 21, include that when a piece of cataract occludes the phaco tip, vacuum will build up in the aspiration line. When that occluded piece is emulsified, there still will be a vacuum in the aspiration line and a surge will be created thus reducing the intraocular pressure. When a pressure transducer in the aspiration line detects a rapid change in vacuum the valve in the handpiece, can be instantaneously closed and a release of sterile fluid in the aspiration line can occur to remove the vacuum and the handpiece valve can then reopen. This valve, by closing instantaneously and opening immediately after fluid is released into the aspiration line will prevent surges of intraocular pressure.

Referring now to FIGS. 28 and 29, a handpiece assembly 11 that includes a collapsible silicone membrane 22 is illustrated. The silicone membrane 22 is disposed radially outside of the needle 16 and defines an annular reservoir chamber 24 disposed between the silicone membrane 22 and needle 16. The reservoir is in fluid communication with the infusion fluid as it passes through the handpiece assembly and out through the infusion sleeve port near the needle tip. The silicone membrane is made from a soft elastic material so that the membrane 22 can collapse during an aspiration surge during use of the ultrasonic handpiece. Typically, when an aspiration surge occurs the relatively large amount of fluid within reservoir 24 is of a sufficient volume so that this fluid can be immediately withdrawn from the reservoir and introduced into the intraocular area, which results in an immediate compensation for the fluid lost from the surge. As is well known, a drop in intraocular pressure can cause considerable problems such as collapse of the intraocular tissue onto the vibrating phaco needle. Accordingly, the reservoir 24 is designed to provide additional infusion fluid in the intraocular area as soon as an aspiration surge occurs. The reservoirs is located immediately adjacent to the needle tip to minimize the time it takes to replace the intraocular fluid. The surge will cause a decrease of intraocular pressure and will therefore provide a suction effect to withdraw the fluid contained within reservoir 24. This suction effect causes the membrane 22 to collapse, as illustrated in FIG. 29. An air vent 26 is provided radially outside of the silicone membrane 22 to permit membrane 22 to collapse freely.

Figure 31:
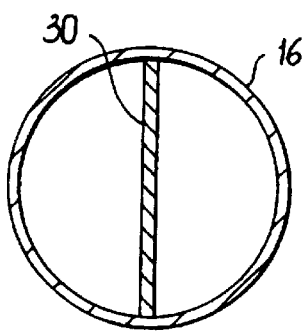
FIG. 31 is a front view of a phacoemulsification needle employing one of the different configurations of barriers and baffles.
Figure 32:
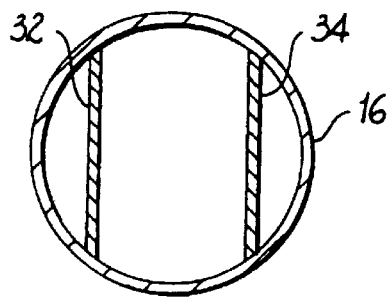
FIG. 32 is a front view of a phacoemulsification needle employing one of the different configurations of barriers and baffles.
Figure 33A:
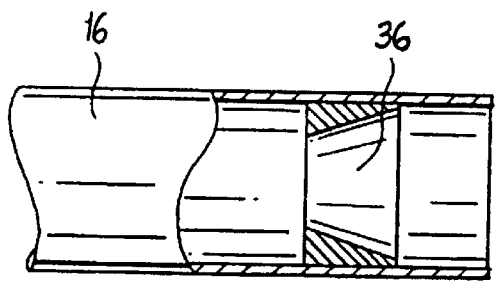
FIGS. 33A–B, 34A–B, 35A–B, 36A–B, 37A–B and 38-42 show various shape barriers which can be placed on the inside or outside of the needle
Figure 33B:
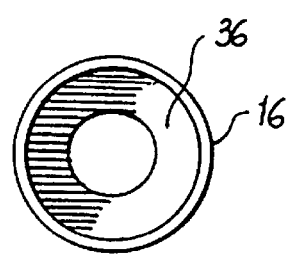
Figure 34A:
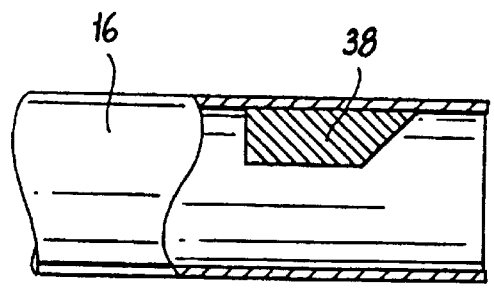
Figure 34B:
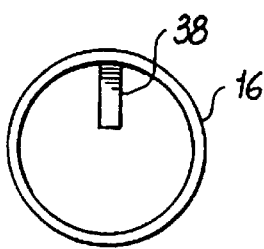
Figure 35A:
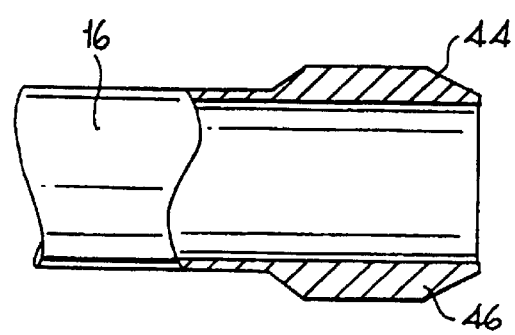
Figure 35B:
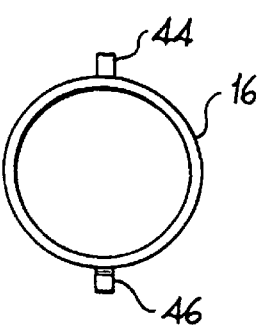
Figure 36A:
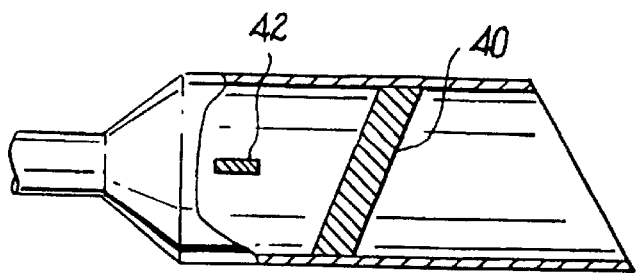
Figure 36B:
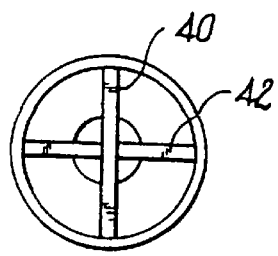

Referring now to FIGS. 30–42, a series of barriers are illustrated, which are attached to the walls of the ultrasonic needle 16. The barriers permit limited or no occlusion at the tip of the needle to enhance emulsification of tissue. As discussed above, occlusion of the tip can create a surge of fluid flow upon break up of the tissue causing the occlusion. This surge in fluid flow can cause a collapse of the intraocular pressure within the eye which is a condition that should be avoided. In addition, the barriers also provide an additional ultrasonic cutting surface to enhance the cutting and emulsification ability of the tip. The barriers are structural members, such as bars, baffles, wedges, etc. which are attached to the walls of the needle 16. A barrier 28 is illustrated in FIG. 30. Other embodiments of barriers including a single bar 30 disposed in the center of the needle or double bars 32, 34 disposed about the center of the needle are illustrated in FIGS. 31 and 32, respectively. The bars 30, 32, 34 prevent nuclear tissue from penetrating into the tip beyond a predetermined amount. Other embodiments of barriers are illustrated in FIGS. 33A–42. For example, in FIGS. 33A and B, an annular ramp shaped barrier 36 is disposed within the tip 16. A wedge shaped plate barrier 38 which does not extend fully across the inside of the tip is illustrated in FIGS. 34A and B. A pair of spaced apart bars 40, 42 are illustrated in FIGS. 36A and B. A barrier 44, 46, illustrated in FIGS. 35A and B, is disposed on the outer surface of sleeve 16. These barriers 44, 46 do not assist in preventing an occlusion, but they do provide an additional surface from which ultrasonic energy can be generated. Other barrier embodiments are illustrated in cross-section in FIGS. 38 and 42. Clearly, almost any type of geometric shape can be used to assist in permitting a limited occlusion of the tip and to aid in emulsifying tissue.

Figure 37A:
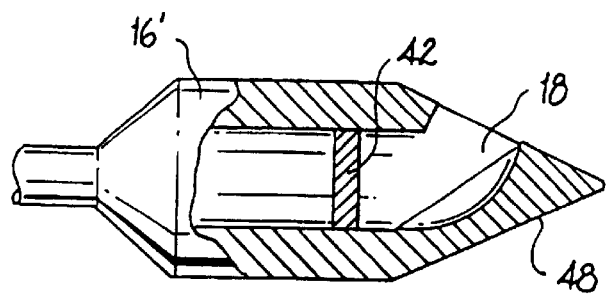
Figure 37B:
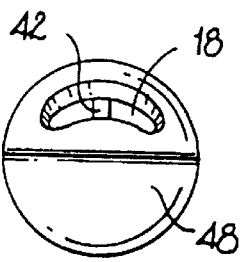
Figure 38:
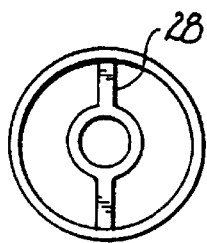
Figure 39:
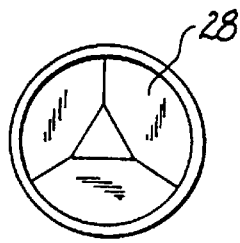
Figure 40:
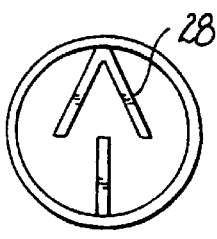
Figure 41:
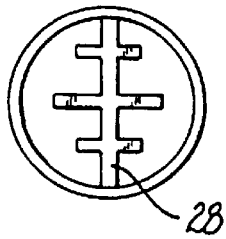
Figure 42:
Figure 43:
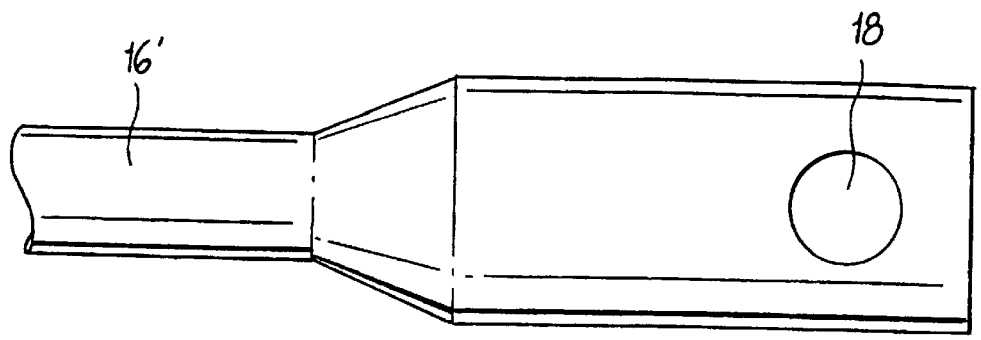
FIGS. 43 and 44 show a top and side view of a needle having a single aspiration hole and specially designed internal and external surfaces to enhance the emulsification and the aspiration effect.
Figure 44:
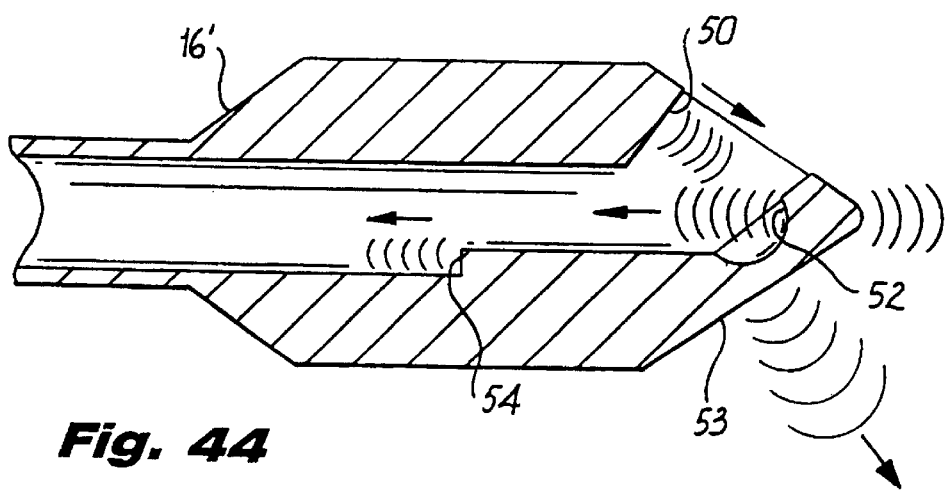

Referring now to FIGS. 37A and B, barrier 42 is illustrated for use in a modified tip 16'. Tip 16' has a wedge shaped distal end surface 48 which provides a large metallic surface area for ultrasonically cutting tissue. The ultrasonic energy from surface 48 is directed in an opposite direction with respect to the aspiration port 18. A tip similar to the one illustrated in FIGS. 37A and B is illustrated in FIGS. 43 and 44. The angled surface 50 disposed inside of the needle 16' can be used to focus energy towards the aspiration port 18, but within the needle 16', to aid in the emulsification of tissue. Other surfaces within that needle including surface 52 and a stepped shoulder surface 54 assist in the suction of the nuclear tissue after it has been emulsified. Surface 52 also is disposed within the line of ultrasonic energy that has been generated from surface 50 to effectively prevent this energy from causing damage to the surrounding tissue. Surface 52 is preferably a spherical surface, and can simply be formed by drilling a blind bore into the shaft 16'. Surface 52 would be the distal portion of the blind bore. Exterior surface 53 is a blunt surface which emits ultrasonic energy at a sufficient energy level to be able to split the cataract. However, the energy generated by surface 53 dissipates quickly so as to minimize the risk of damaging to the posterior capsule.

Figure 45:
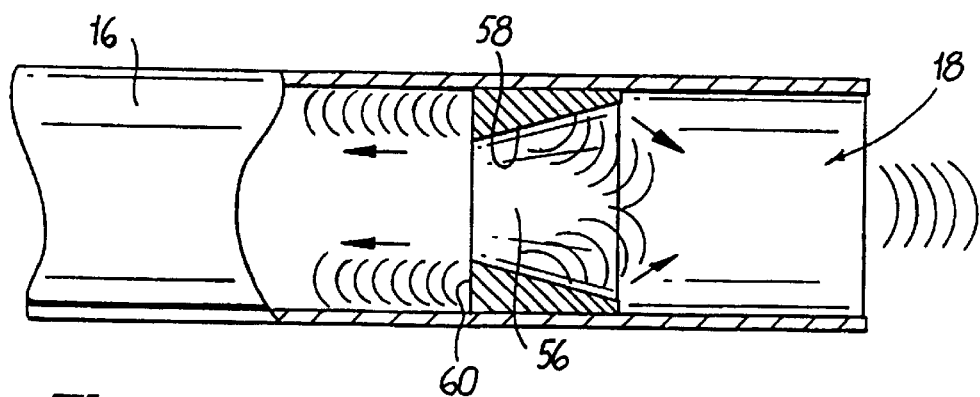
FIG. 45 shows a barrier similar to the embodiment illustrated in FIGS. 33A–B but with the barriers set further back within the needle.

FIG. 45 illustrates a needle that includes a ramp shaped annular barrier 56 whose ramp shaped surface 58 is directed towards the needle tip to focus ultrasonic energy across the aspiration port 18. The stepped rear shoulder surface 60 of the ramp 56 is used to assist in the suction of the nuclear tissue after it has been emulsified. In most uses it is desirous to contain the ultrasonic energy within the needle to minimize the ultrasonic radiation which can cause damage to the intraocular tissue. In the embodiment illustrated in FIG. 45, ultrasonic energy generated by ramp surface 58 is prevented from exiting the needle by the needle's interior surface.

The present inventors have found the use of steps, angles, and barriers within the ultrasonic needle useful to focus ultrasonic energy across the aspiration port to aid in emulsifying nuclear tissue and to aid in pushing emulsified material in the direction of the aspiration flow.

Figure 46:
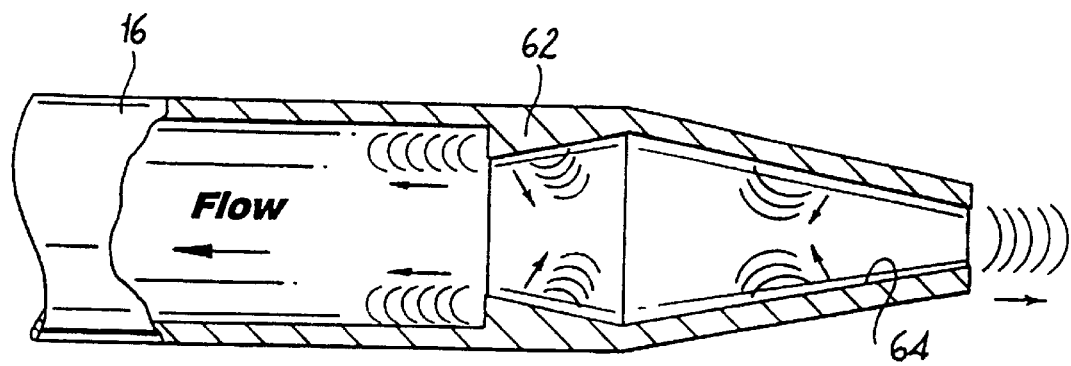
FIGS. 46 and 47 illustrate various barrier shapes and steps disposed within the needle to enhance the emulsification and aspiration.

FIGS. 46–50 illustrate various embodiments of needle tips which achieve these results. FIG. 46 illustrates a tapered needle 16 that has an internal annular shaped ramp 62 similar to ramp 56 illustrated in FIG. 45. In addition, the front tapered end surface 64 of the needle 16 also radiates ultrasonic energy within the internal area of the tip to assist in the emulsification of nuclear tissue.

Figure 47:
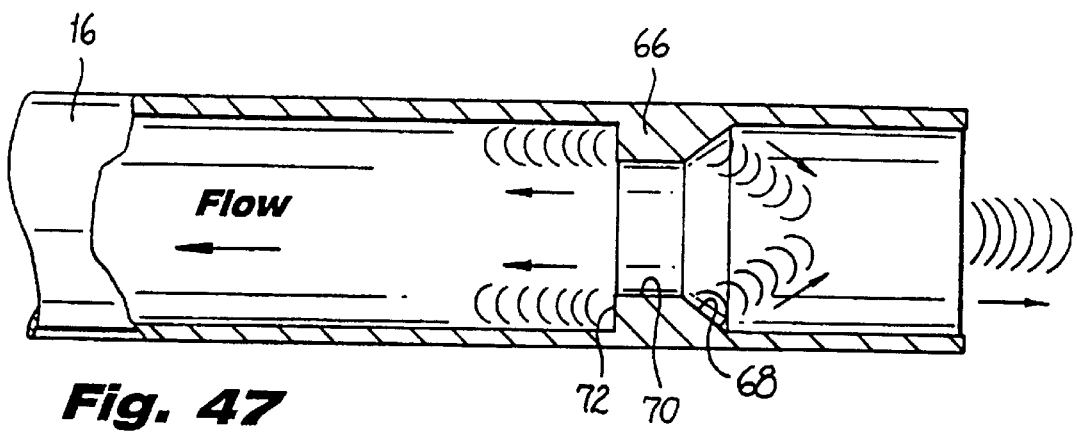

FIG. 47 illustrates an annular shaped ramp surface 66 that has a forwardly directed ramp surface 68, a reduced diameter passageway 70, and a stepped shoulder surface 72. Ramp surface 68 emits ultrasonic energy to aid in the emulsification of tissue, whereas shoulder surface 72 emits ultrasonic energy to assist in the suction of the emulsified tissue.

Figure 48:
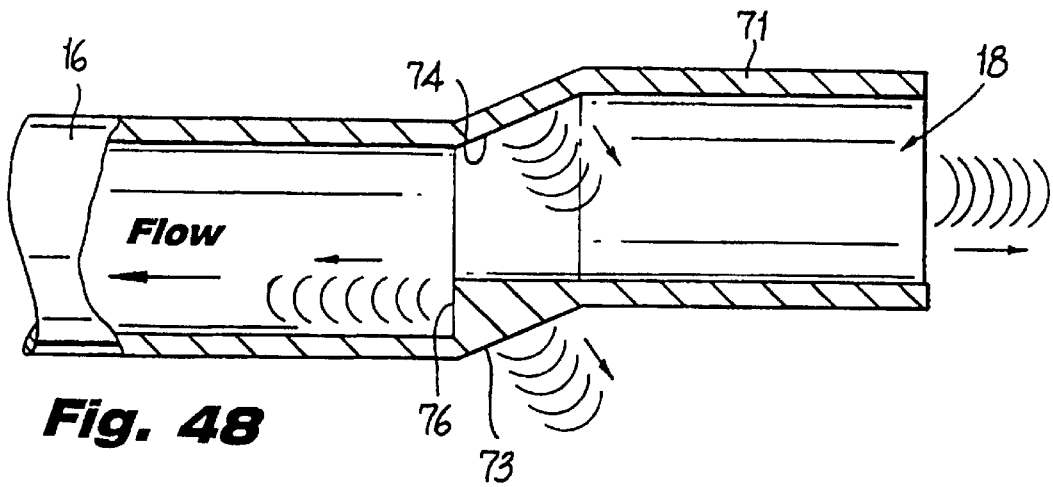
FIG. 48 illustrates a stepped needle which enhances emulsification and the aspiration effect.

FIG. 48 illustrates a needle tip 16 that has the tip end 71 off-center (i.e., not concentric) with respect to the main portion of the tip 16. An internal ramp surface 74 emits ultrasonic energy adjacent to the aspiration port 18 to assist in the emulsification of nuclear tissue. A stepped shoulder surface 76 assists in the suction of that emulsified tissue by generating ultrasonic waves in the direction of flow. Additionally, an external ramped surface 73 emits ultrasonic energy to aid in the cutting and emulsifying of nuclear tissue.

Figure 49:
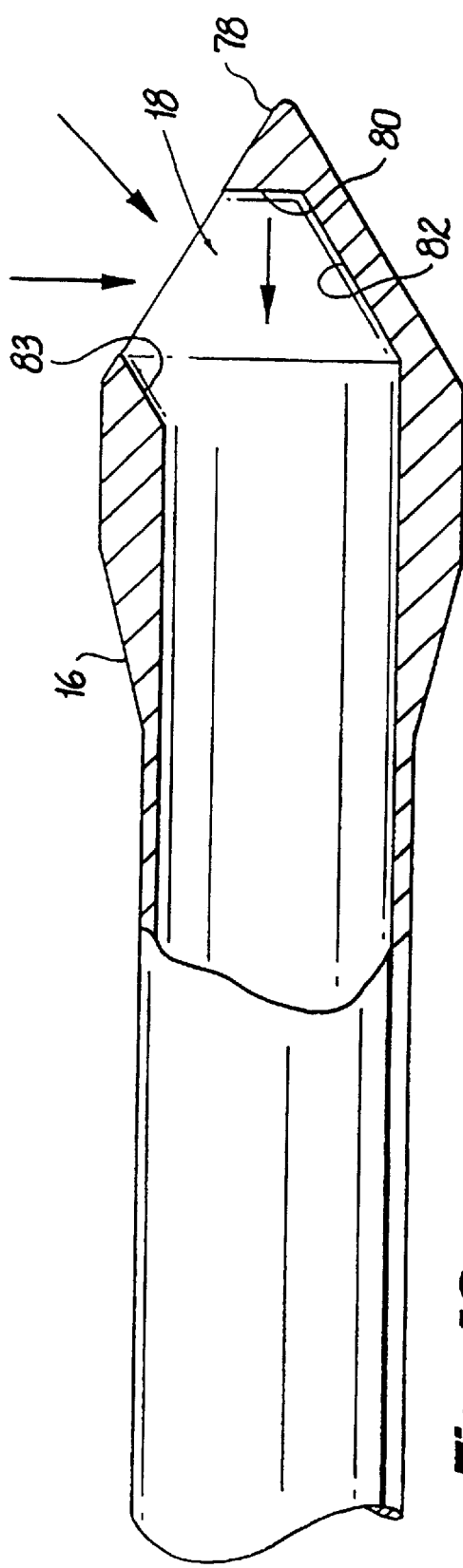
FIGS. 49 and 50 are sectional views of additional embodiments of needle tip.

FIG. 49 illustrates a needle tip 16 that has a wedged shape front tip surface 78. Surface 78 emits ultrasonic energy outside and forward of the tip end to assist in the cutting of nuclear tissue. In addition, a shoulder surface 80 disposed adjacent to the aspiration port 18 assists in pushing the material into the interior of the needle tip 16. Internal surfaces 82, 83 also emit ultrasonic radiation energy to assist in the emulsification of nuclear tissue.

Figure 50:
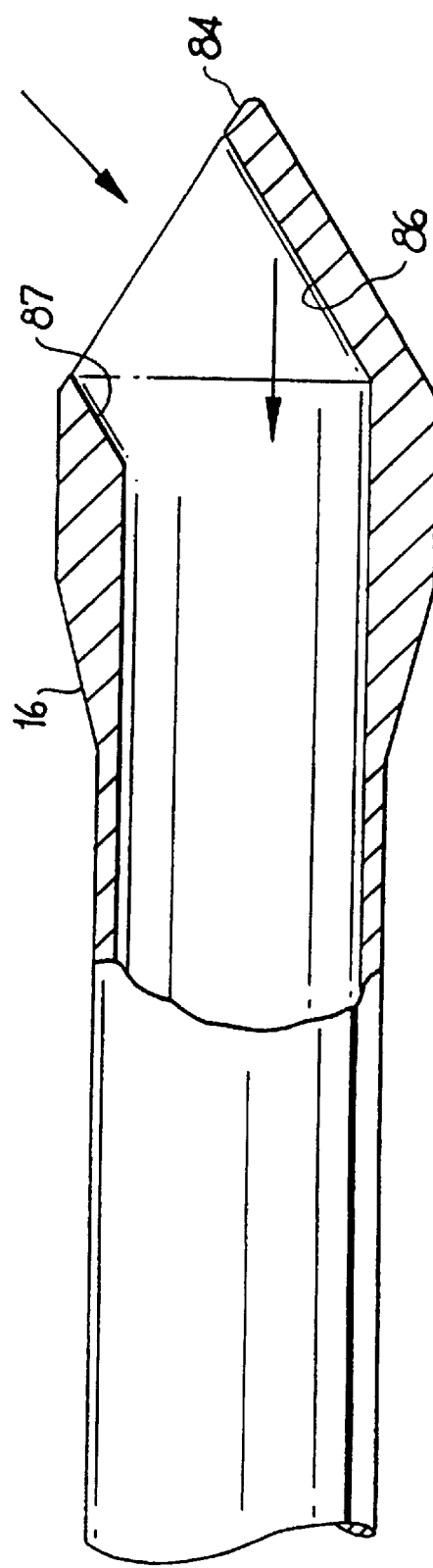

FIG. 50 illustrates an embodiment similar to that illustrated in FIG. 49 in that a front wedged shape surface 84 and ramp surfaces 86, 87 are utilized in a similar manner to surfaces 78, 82 and 83 in the embodiment illustrated in FIG. 49.

Referring now to FIGS. 51 and 52. A compressible sleeve 88 is illustrated. Sleeve 88 includes an accordion section 90 to permit the sleeve 88, once it is connected to the handpiece 11 (not shown in FIGS. 51 and 53) at area A, to move axially with respect to the handpiece. Sleeve 88 is connected to the handpiece by a fluid tight connection, which permits the handpiece 11 to rotate freely with respect to the sleeve 88. When the tip end of the needle 16 is inserted into the incision 14 of the cornea 16, the forward end 92 of the sleeve 88 extends through the corneal surface 16, such that forward end 92 substantially matches to the incision 14 in the cornea. Due to the accordion design and to the rotational coupling, the handpiece and needle can be manipulated to a limited extent in the axial direction and rotated freely about the longitudinal axis while the sleeve 88 will remain stationary with respect to the cornea 16. Thus, this forward portion 92 of the sleeve acts similar to a plug to completely seal the incision in the cornea. In addition, the infusion port at the distal end of the sleeve 92 is located near the cornea and away from the aspiration hole 18 of the needle. Thus, there is considerably less turbulence within the eye which provides for better aspiration of emulsified tissue. In other words, if the infusion port is located too close to the aspiration port, the fluid will naturally follow a path of least resistance and short circuit directly from the infusion port to the aspiration port, which clearly reduces the amount of tissue that can be removed from the eye or at the very least reduces the amount of time it takes to remove the desired amount of tissue from the eye.

Having described the presently preferred exemplary embodiment of a new and improved phacoemulsification handpiece, sleeve, and tip, in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

I claim:

1. An ultrasonic surgical instrument for supplying infusion fluid from a source to an operating to be accessed through an opening in a wall, emulsifying tissue from the operating site with ultrasonic energy and removing material from the site by an aspiration flow force from a source comprising:
   a generator of ultrasonic energy;
   a needle for receiving the ultrasonic energy, said needle having an aspiration inlet port formed by an opening in only one side of the needle at the needle distal end at an angle to the needle longitudinal axis to be placed in the area of the operating site and an internal aspiration flow passage to which the aspiration flow force is applied to aspirate tissue into said opening of said aspiration inlet port; and
   a sleeve surrounding at least a portion of said needle and spaced therefrom for fitting into the opening to the operating site and having an outer portion of compressible material to be engaged by and compressed by the wall to conform to the opening and having a reinforcing member interior of said outer portion to prevent collapse of said sleeve against said needle, the space between said needle and said sleeve for receiving the infusion fluid and having at outlet port for supplying the infusion to the operating site.

2. An ultrasonic instrument as in claim 1 wherein the opening in said surrounding wall transverse to the needle longitudinal axis forming said aspiration inlet port is of circular or rectangular shape.

3. An ultrasonic instrument as in claim 1 wherein said aspiration inlet port opening is at an angle of from greater than 0° and up to 90° relative to the needle longitudinal axis.

4. An ultrasonic instrument as in claim 1 wherein the opening which defines the aspiration inlet port on the distal end of the needle is one of a conical surface, a surface which is a partial sphere or a surface in the shape of a tetrahedron.

5. An ultrasonic instrument as in claim 1 wherein said opening is in the shape of one of a polygon, a triangle, two triangles aligned along the needle longitudinal axis, a circle, two triangles each having a base which is prallel to the needle longitudinal axis, or two circles.

6. An ultrasonic instrument as in claim 1 wherein said aspiration inlet port opening in the needle wall is transverse to the needle longitudinal axis and the needle extreme distal end is open a form a second port inlet to said needle internal aspiration flow passage.

7. An ultrasonic instrument as in claim 1 wherein said opening transverse to the needle longitudinal axis is in the shape of one of an oval, a triangle, two triangles each having a base which is parallel to the needle longitudinal axis, a polygon, or a diamond with apices parallel to the needle longitudinal axis.

8. An ultrasonic instrument as in claim 1 wherein said needle distal end in which said opening is formed is a surface which is a part of a tetrahedron that is offset from the needle longitudinal axis.

9. An ultrasonic instrument as in claim 1 wherein the distal end of said needle which applies the ultrasonic energy to the operating site is one of a surrounding wall forming an opening at the extreme distal end which defines a second aspiration inlet port and said aspiration inlet port opening is in said surrounding wall transverse to the needle longitudinal axis, a surrounding wall forming an opening at the extreme distal end which defines a second aspiration inlet port with said surrounding wall having a cutout on a part of the distal extreme end edge forming said aspiration port inlet opening, a conical surface with the apex of the conical surface at the distal end of the needle and an opening in said conical surface forming said aspiration inlet port opening, a surface of a part of a sphere and an opening in said part spherical surface forming said aspiration inlet port opening, and a surface of a tetrahedron of wedge shape with the narrow end of the wedge at the needle extreme distal end and an opening in said surface forming said aspiration inlet port opening.

10. A surgical instrument comprising:
    an operating tool to pass through an opening in a wall to work on an operating site and to be engaged by the wall;
    a generator of ultrasonic energy for supplying the ultrasonic energy to the tool to be applied from the tool distal end to the operating site to emulsify tissue at the operating site; and
    a sleeve surrounding at least a portion of said tool for fitting into the opening to the operating site and to be spaced from said tool at least in the area where said sleeve is engaged by the wall, said sleeve having an outer portion of compressible material to be engaged by and compressed by the wall forming the opening to conform to the shade of the opening and having a reinforcing member interior of said outer portion to prevent collapse of said sleeve by the wall against the tool.

11. A surgical instrument as in claim 10 wherein said reinforcing member comprises a plurality of strands of rigid material embedded within said sleeve.

12. A surgical instrument as in claim 11 wherein said reinforcing member strands comprises at least one of the materials of plastic, synthetic fibers and a metallic based material.

13. A surgical instrument as in claim 10 wherein said sleeve of compressible material is of at least one of silicone, rubber and plastic.

14. A surgical instrument as in claim 10 wherein said reinforcing member comprises a spiral of rigid material embedded in said sleeve.

15. A surgical instrument as in claim 14 wherein said spiral of rigid material comprises at least one of the materials of plastic, synthetic fibers and a metallic based material.

16. A surgical instrument as in claim 14 wherein said sleeve of compressible material is of at least one of silicone, rubber and plastic.

17. A surgical instrument as in claim 10 wherein said sleeve has an internal portion for receiving infusion fluid and an outlet port extending through said sleeve for supplying the infusion fluid to the operating site.

18. A surgical instrument as in claim 17 wherein said infusion outlet port is in the shape of one of a circle, oval and ellipse.

19. A surgical instrument as in claim 10 wherein said tool has an internal aspiration flow passage having an inlet port at the tool distal end, an aspiration flow force applied in said flow passage aspirating tissue from the operating site into said inlet port to be emulsified by the ultrasonic energy.

* * * * *